United States Patent [19]

Wittmaier et al.

[11] 4,366,821

[45] Jan. 4, 1983

[54] BREATH MONITOR DEVICE

[75] Inventors: Edward A. Wittmaier, St. Charles; Joseph A. Kretschmer, St. Ann, both of Mo.

[73] Assignee: Marie C. Kercheval, St. Charles, Mo.

[21] Appl. No.: 187,503

[22] Filed: Sep. 15, 1980

[51] Int. Cl.$^3$ ............................................. A61B 5/08
[52] U.S. Cl. .................................. 128/719; 128/724; 340/573
[58] Field of Search ............... 128/724, 716, 718, 719, 128/721, 722, 723, 724, 204.23, 204.22; 340/573

[56] References Cited

U.S. PATENT DOCUMENTS

| | | | |
|---|---|---|---|
| 2,831,181 | 4/1958 | Warner | 128/724 |
| 3,316,902 | 5/1967 | Winchel et al. | 128/724 X |
| 3,414,896 | 12/1968 | Glick et al. | 340/573 X |
| 3,643,652 | 2/1972 | Beltran | 128/725 |
| 3,802,417 | 4/1974 | Lang | 128/724 X |
| 3,903,875 | 9/1975 | Hughes | 128/724 |
| 3,913,379 | 10/1975 | Rusz et al. | 128/719 X |
| 3,962,917 | 6/1976 | Terada | 128/725 X |
| 3,991,304 | 11/1976 | Hillsman | 128/725 X |
| 3,999,537 | 12/1976 | Noiles | 128/724 |
| 4,187,842 | 2/1980 | Schreiber | 128/202.22 |

OTHER PUBLICATIONS

Chess et al., Medical and Biological Engineering, Jan. 1976, pp. 97-100.

Primary Examiner—Kyle L. Howell
Assistant Examiner—John C. Hanley
Attorney, Agent, or Firm—Haverstock, Garrett & Roberts

[57] ABSTRACT

A breath monitor device useful for monitoring the inhaling and exhaling of patients and particularly patients on a breathing apparatus, the device being constructed to have a sensor element positioned in the path of the breath flow to respond to the breath and to the constituants thereof, the breathing apparatus including structure for supporting the sensor element, and a control circuit connected to the sensor element including a circuit portion for amplifying responses produced by the sensor element, a circuit portion for establishing threshold conditions for indicating whether the individual patient being monitored is inhaling or exhaling and that the patient is using the oxygen being breathed at a set minimum rate, a control panel connected to the control circuit including a first indicator for indicating when the patient is inhaling, a second indicator for indicating when the patient is exhaling, and a control element adjustable to establish minimum safe breathing rate conditions including an alarm device for producing an alarm condition when a breathing rate being monitored either falls below the minimum safe rate or ceases indicating a respiratory blockage or breathing failure. A counter circuit for counting the breath rate of the patient is also provided.

51 Claims, 5 Drawing Figures

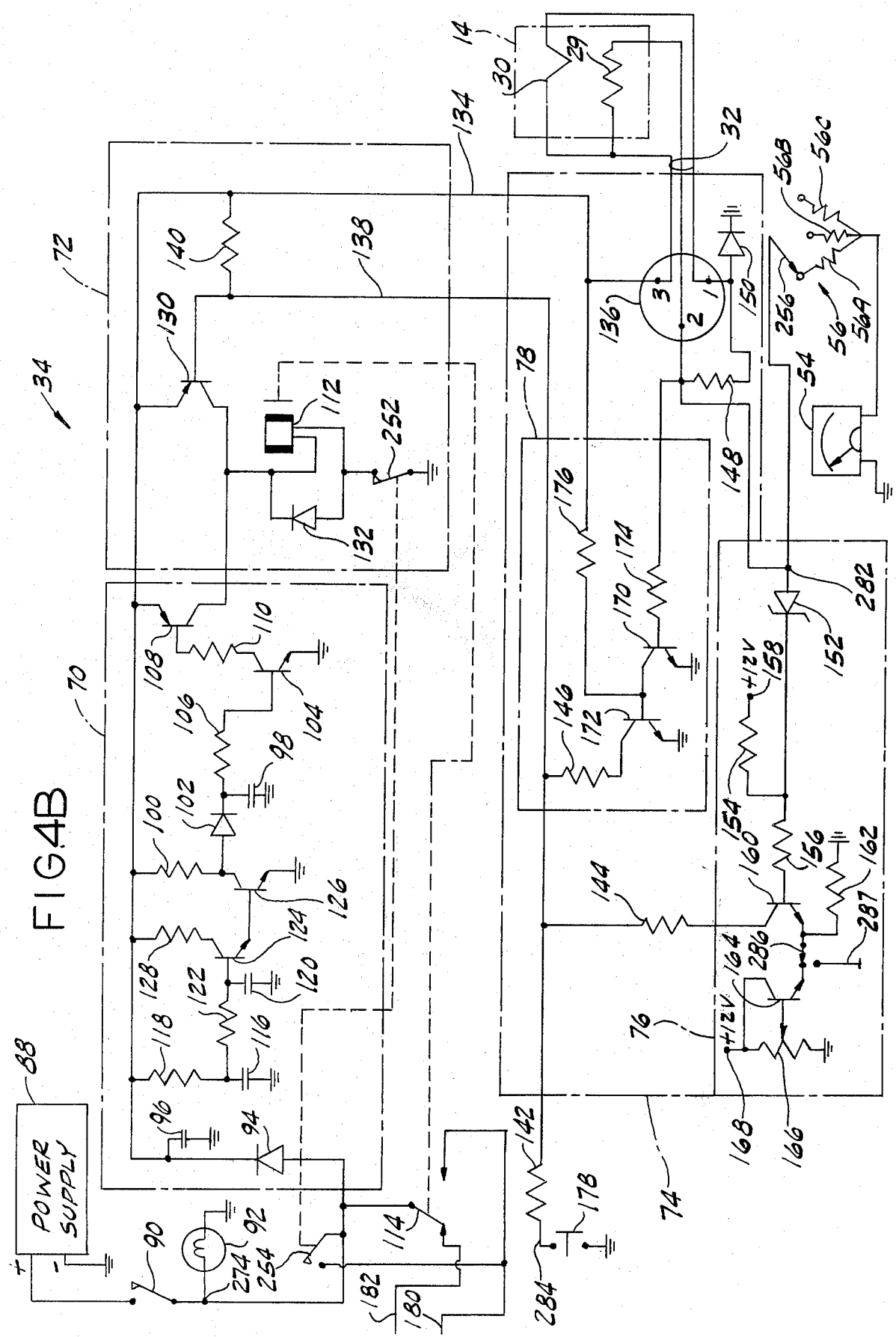

BREATH MONITOR DEVICE

BACKGROUND AND SUMMARY OF THE INVENTION

Breathing apparatus such as tracheal and endotracheal tubes and oxygen masks are frequently used to facilitate the breathing or persons in distress. In such cases it is important to be able to monitor the breathing during exhaling and inhaling including monitoring the breathing rate and the composition of the breath to know if the person is receiving sufficient breath, to know if the breath rate, i.e. number of breaths per minute is being maintained or if the breathing rate during inhaling and during exhaling should fall below some minimum safe rate and to know that the person is receiving an accepted rate of oxygen. It is also important for the doctor or nurse to be able to establish minimum breathing conditions for each patient taking into account the patient's history and physical condition, and it is important to be able to reassess a breathing rate from time-to-time to take into account different factors such as the patient's ability to use free oxygen in the air the patient is breathing. The present device has these and other capabilities and also includes means which enable a doctor or nurse to be continuously made aware at the bedside or at a remote location of the patient's breathing and changes in breathing and it enables periodic adjustment of the monitored conditions to take into account changes that occur. The present device also includes means to produce an alarm if the breathing rate deteriorates below some preestablished condition and this can be adjusted taking into account the condition of the patient. The present device is therefore a very sensitive and versatile monitor which is relatively easy to adjust and use.

The present device is useful in monitoring various breathing conditions of patients such as apnia in which the patient ceases to breath, the breath rate of the patient, and cachypneic in which the patient begins to breath too rapidly. The monitoring of the breathing conditions is particularly useful in the treatment of various conditions and diseases such as emphysema, stroke, drug overdose, sleep apnia in children and pulmonary embolus.

It is therefore a principal object of the present invention to provide accurate adjustable means for monitoring the breath, breath rate and breath composition and especially of persons equipped with breathing apparatus such as tracheal tubes.

Another object is to be able to continuously and selectively monitor the exhaling and inhaling of a person.

Another object is to provide a breathing monitor instrument especially for use in hospitals and other places where the vital functions are monitored.

Another object is to provide a breathing monitor instrument for monitoring the breath, breath rate and breath composition at a location remote from the patient being monitored.

Another object is to increase the information that is available about persons who have breathing difficulties.

Another object is to provide a relatively inexpensive yet highly reliable breath monitoring device which can be used to monitor the breathing of persons whose normal breathing function may be impaired or obstructed for some reason.

Another object is to provide means for monitoring the breathing functions which can be adjusted to establish desired minimum safe breathing rate conditions, and to produce an alarm under conditions that can be selected and adjusted as desired.

Another object is to establish separate minimum conditions and criteria for inhaling and exhaling to produce alarm conditions.

Another object is to establish a predetermined delay period before an alarm will be produced to indicate that a particular condition of a persons' breathing represents a danger.

Another object is to provide a breath monitor of the breath.

Another object is to provide a device capable of separately monitoring the chemical composition and breathing rate during inhaling and exhaling.

Another object is to provide a breath monitoring device that can operate compatibly with other devices used to assist the breathing.

Another object is to provide a breath monitoring device that provides a warning if the breath sensor element becomes disconnected or fails in either the shorted or open condition.

BRIEF DESCRIPTION OF THE DRAWINGS

These and other objects and advantages of the present invention will become apparent after considering the following detailed specification which discloses a preferred embodiment of the subject breath monitor device on conjunction with the accompanying drawings, wherein;

FIGS. 4A and 4B together show a schematic circuit diagram of a control circuit for the present breath monitor means.

DETAILED DESCRIPTION OF THE INVENTION

Figure 1:
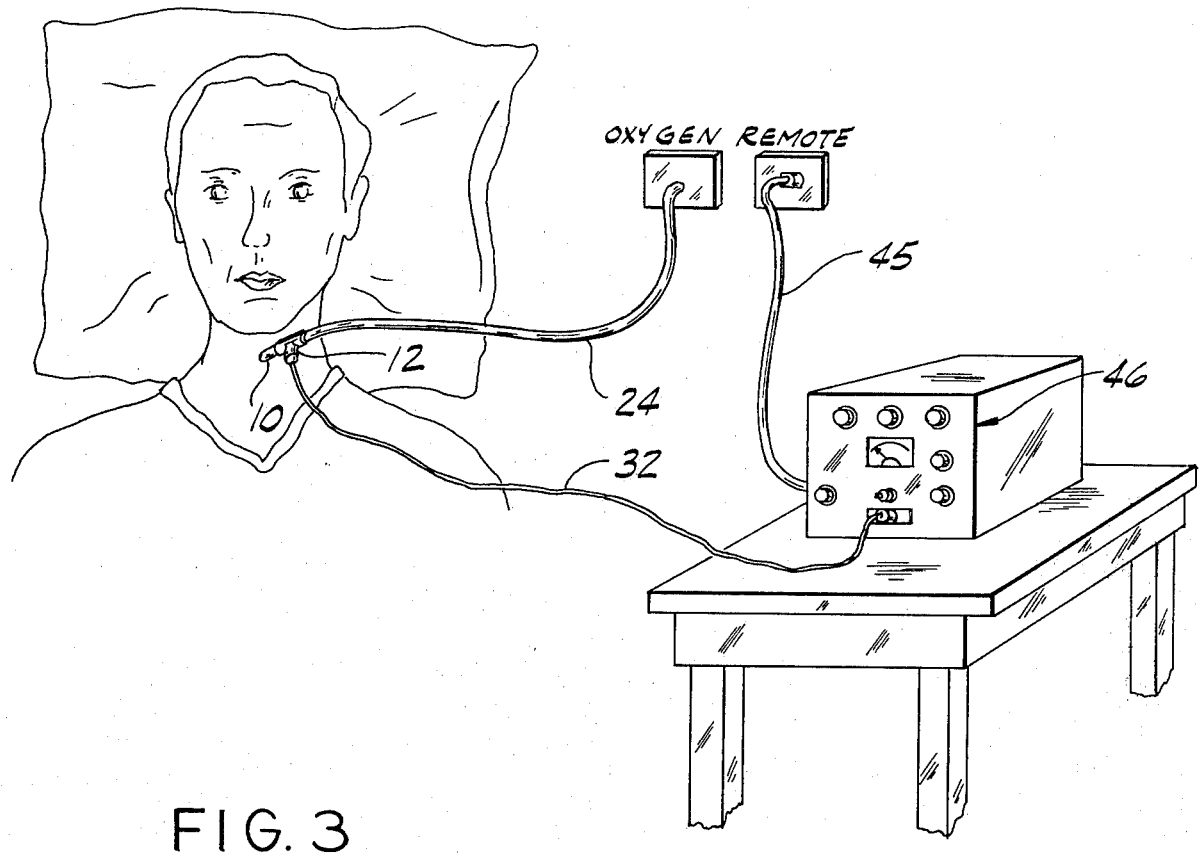
FIG. 1 is a perspective view of a person on a tracheal tube equipped with an adapter for accomodating a breath responsive sensor element connected to a control device for monitoring breath, all of which are constructed according to the present invention.

Referring to the drawings more particularly by reference numbers, number 10 refers to a tracheal or endotracheal tube equipped with an adapter 12 for accommodating a sensor element 14 used to monitor the breath of a person equipped with the tube 10. The construction and operation of the tracheal (or endotracheal) tube 10 may be conventional and are not part of the present invention as such except in so far as they provide a means for the controlled passage of air past, adjacent, or through the sensor 14 during inhaling and exhaling. An oxygen or other like mask could likewise be constructed with an adaptor having means for controlled passage of air past or through the sensor during inhaling and exhaling breath. This is necessary for best operation of the present device because the inhaling and exhaling breath must move by, through and adjacent to the sensor device 14 for the device to operate most effectively. A mask can also be constructed for a patient receiving nasal oxygen wherein the mask has means for holding the sensor 14 wherein the breath of the patient moves over the sensor 14 when the patient exhales. It is also important to the operation of the present device to be able to adjust the sensitivity of the device to establish threshold conditions tailored to each particular person whose breath is being monitored. For example, different persons such as smokers and non-smokers will have different breath characteristics including different breathing rates and different breath composition all of which will effect the sensor 14. These and other factors can be taken into account by the subject monitor by properly setting or adjusting the various controls as will be explained. A remote connector 45 may also be provided for transmitting monitoring and warning signals to a remote location.

Figure 2:
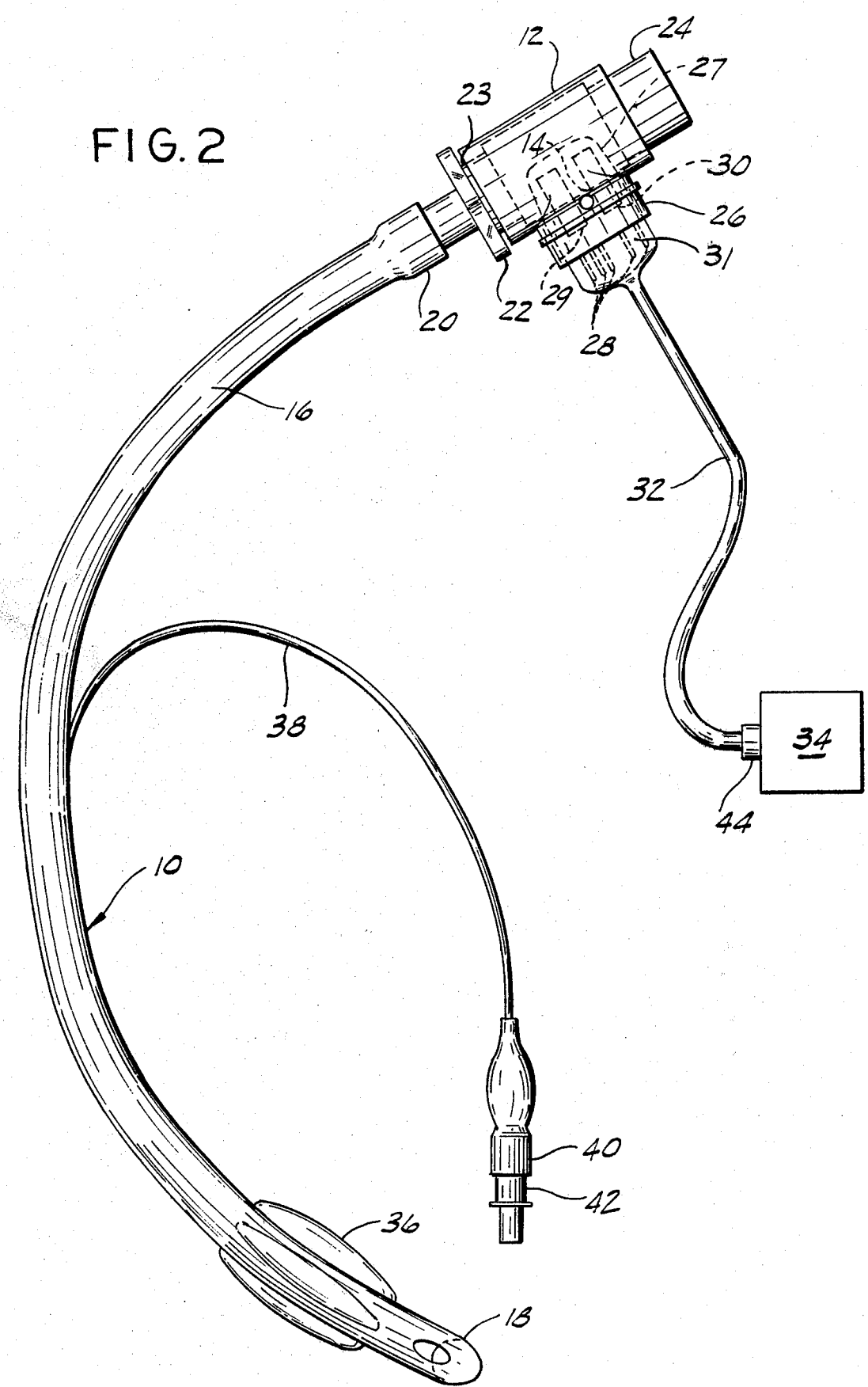
FIG. 2 is an enlarged cross-sectional view showing the details of a tracheal tube and an adapter for a sensor element for use therewith.

Referring to FIG. 2, the tracheal tube 10 is shown including an elongated curved open ended tubular portion 16 which has one end 18 that is constructed to be positioned in the throat or other breathing passage. The tube 10 has an opposite end 20 which is connected to a tubular fitting member 22. The fitting 22 has an enlarged tubular portion 23 which extends into one end of the T shape adapter 12, and the opposite end of the adapter 12 is connected to a source of air or oxygen such as to oxygen supply line 24. The adapter 12 also has a sidewardly extending tubular portion 26 which has an inside diameter that is large enough to receive the sensor element 14 as shown in dotted outline in FIG. 2. The sensor element 14 should extend far enough into the adaptor portion 26 to be in the stream of air flowing through the tracheal tube 10. The sensor 14 may have a screen or perforated portion 27 which surrounds a sensor element which element may be of a known construction. The sensor 14 also has a resistive element 29 and a heater element 30 having electrical connection prongs 28 which cooperate with female connection means in socket member 31. The socket 31 is in turn connected by leads 32 to another connector member 44 which connects the leads 32 to control circuit 34 for the subject device (FIGS. 4A and 4B).

The tracheal tube 10 may be of a commercially available construction including having an inflatable collapsible plastic sleeve portion 36 which communicates through a small tube 38 and a fitting 40 with a one way valve 42. When the fitting 40 is connected to a source of air it inflates the inflatable sleeve 36. This is done so that when the tracheal tube 10 is positioned in the throat, leakage thereby will be prevented. This is common practice with commercially available tracheal tubes, and is not part of the present invention as such.

The present device includes a control panel 46 (FIG. 3) positioned at a convenient location taking into account the circumstances and location of the person whose breath is to be monitored. This will usually be near the bed of the person or at some remote location such as at a nurses' station. The control panel 46 includes a number of dials, indicators and switches including a lighted power switch 48 for turning the device on and off, which switch is illuminated whenever power is being supplied to the device. The control panel 46 also has an exhale indicator light 50 which, when the panel is in a monitoring mode and properly adjusted, is illuminated whenever the person being monitored is exhaling, and an inhale indicator light and associated test switch 52, labeled Inhale/Test, which device is illuminated whenever the patient is inhaling. The switch portion of the indicator light and test switch 52 controls a normally open switch which, when closed, tests the relay circuit of the control circuit 34 as will be explained later. A meter 54 and an associated meter scale control 56 shown as a knob having three setting positions labeled 3, 4, and 6 are mounted on the control panel 46 and will be described later. Also, another adjustable control 58 is positioned on the panel 46 above the meter scale control 56 and is labeled alarm rate. The control 58 adjusts a pair of potentiometers in the circuit 34 that are used to establish a minimum safe breathing rate below which the person being monitored is considered to be in some danger and should be checked. A rate adjust control 60 is provided to set a threshold for the sensor 14 to differentiate between the composition of gases in the breath of the monitored patient during inhaling and exhaling. A female receptacle 62 for receiving the male plug 44 on the opposite end of the leads or cable 32 is also provided on the control panel 46. An alarm on/off switch 64 is provided on the control panel 46 for deenergizing an alarm device in the circuit 34 and will be described later. The various circuits and circuit connections to the control panel are shown in the schematic circuit diagram of FIGS. 4A and 4B.

Figure 3:
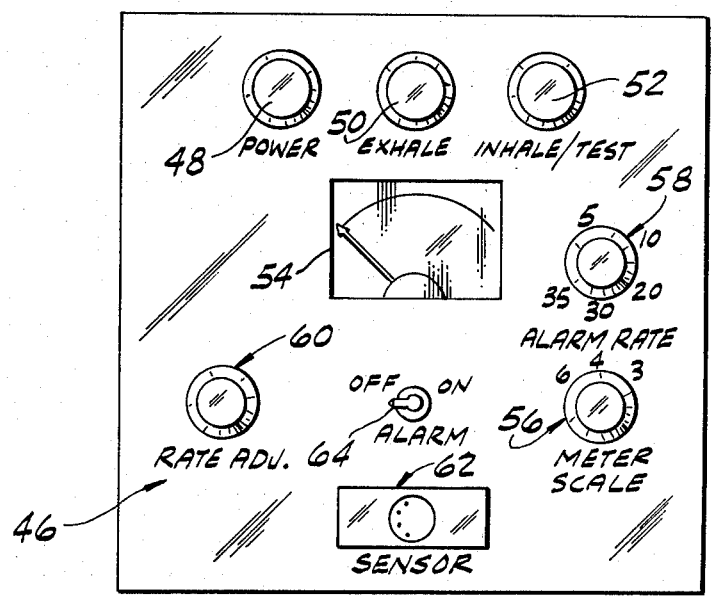
FIG. 3 is a front elevational view of a control panel for use with a breath monitor device constructed according to the present invention.
Figure 4A:
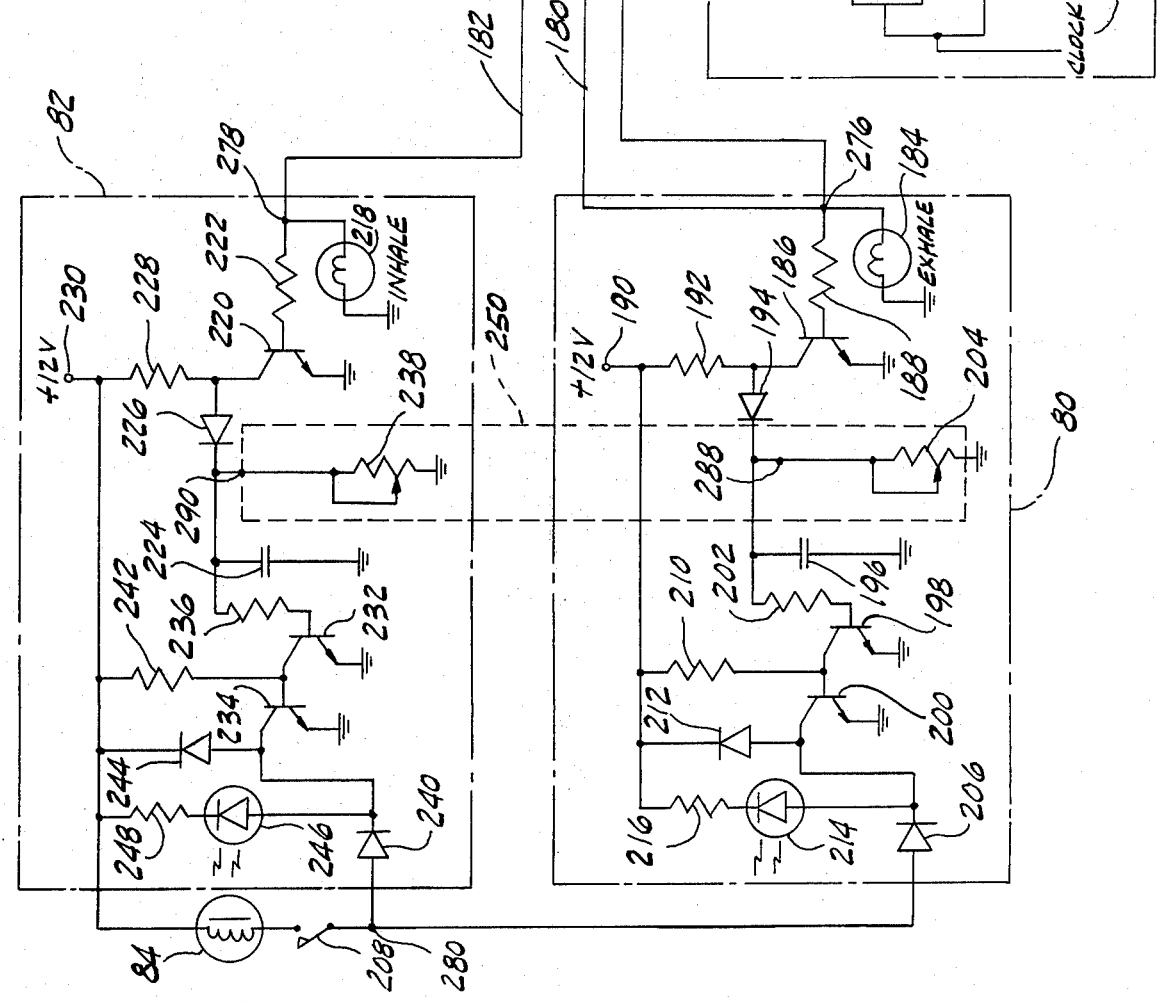

Turning now to FIGS. 4A and 4B, the control circuit 34 has a turn-on circuit 70, a relay circuit 72, a sensor circuit 74 having a voltage comparator circuit 76 and an open-sensor warning circuit 78, an exhale delay circuit 80, an inhale delay circuit 82, an audio warning device or buzzer 84, and a respiration rate counter circuit 86. As will be explained further, the sensor 14 is connected to the sensor circuit 74 and detects gas components present in the breath of a patient to determine if the patient is inhaling or exhaling. This detection activates a relay or similar device in relay circuit 72 to switch the relay from activating one of the delay circuits 80 or 82 to the other. If the state of the relay of the relay circuit 72 is not changed within a preset length of time determined by the setting of the adjustable control 58 of FIG. 3, the last activated delay circuit 80 or 82 will energize and sound the warning buzzer 84.

The voltage comparator circuit 76 compares the output voltage on the sensor 14, which may be a gas sensor, to a threshold voltage which is adjusted by the control 60. The control 60 is therefore provided for adjusting the level of the threshold voltage to a particular level depending upon the chemical composition of the breath of the particular patient being monitored. The control 60 will be set differently for smokers and non-smokers for example. The open-sensor warning circuit 78 is provided to produce an audible warning if the sensor 14 should become disconnected from the socket 31 or if the sensor 14 should fail or become defective in the open circuit condition.

A preferred type of sensor 14 for use with the present device is a gas electric sensor which has a resistive element 29 whose resistance decreases in the presence of certain exhaled gases or upon a depletion of free oxygen in the air around or passing over the sensor 14. The sensor 14 also has the heater element or filament 30 which requires some time period to heat the resistive element 29 for the sensor 14 to become stabilized in ambient air conditions. For this purpose the turn-on circuit 70 is provided to switch the relay circuit 72 from one condition to another for a length of time sufficient to give the gas sensor 14 an opportunity to reach its stabilized condition. After this time period, the relay circuit 72 switches back to its initial condition so that the control circuit 34 may begin its monitoring functions. This switching back of the relay circuit 72 gives a positive indication that the turn-on or warm-up cycle is complete.

The control circuit 34 is powered by a power supply 88 through an on/off switch 90. An incandescent bulb 92 is connected to the on/off switch 90 such that when the circuit 34 is turned on, bulb 92 is illuminated. The switch 90 is the switch portion and its bulb 92 is the light producing portion of the lighted power switch 48 shown in FIG. 3. Power is supplied to the turn-on circuit 70 through a diode 94 which is connected to one side of a grounded capacitor 96 connected to the positive supply. The capacitor 96 is included to shunt noise and other transients to ground. When the switch 90 is closed, another capacitor 98 immediately starts to charge through a resistor 100 and a diode 102 such that a transistor 104, whose base is connected to the positive terminal of the capacitor 98 through a resistor 106, is turned on almost immediately after the capacitor 98 begins to charge. The collector of the transistor 104 is connected to the base of another transistor 108 through a resistor 110 such that the turning on of the transistor 104 also turns on the transistor 108 thereby energizing a relay coil 112 in the relay circuit 72. The energizing of the relay coil 112 switches a movable contact in relay contacts 114 from operation with the inhale delay circuit 82 to operation with the exhale delay circuit 80. The importance of this switchover will be explained more in detail hereinafter.

The turning on of the switch 90 also begins the charging of another capacitor 116 through a resistor 118 and of still another capacitor 120 through resistors 118 and 122. After a predetermined time period as determined by the values of the resistors 118 and 122 and the capacitors 116 and 120, another transistor 124 will turn on thereby also turning on transistor 126. A resistor 128 is included in the circuit to properly bias the transistor 124. The turning on of the transistor 126 grounds the anode of the diode 102 so that the capacitor 98 may no longer be charged. The capacitor 98 thereafter discharges through the base-emitter junction of the transistor 104 to ground. When the capacitor 98 is discharged sufficiently, the transistor 104 will turn off thereby also turning off the transistor 108. This causes the relay coil 112 to be deenergized returning the movable contact of the relay contacts 114 from operation with the exhale delay circuit 80 to operation with the inhale delay circuit 82. The entire time delay required for the turning on of the circuit 70 is usually about 25 seconds following the closing of the switch 90. This can be broken down to about two seconds to charge the capacitor 120 and about 23 seconds to discharge the capacitor 98 and this time period is required to give sensor 14 sufficient time to stabilize. After the initial action of turning on the circuit 70 as previously described, further energizing and deenergizing of the relay coil 112 is controlled by another transistor shown in FIG. 4B as PNP transistor 130. A diode 132 is connected across the terminals of the relay coil 112 to help dissipate stored electro-magnetic energy in the relay coil 112 whenever the relay coil 112 is deenergized.

A positive power supply lead 134 is connected from the relay circuit 72 to terminal 3 of a female sensor connector 136 shown as female receptacle 62 in FIG. 3. A control lead 138 extends from the base of the transistor 130 to the sensor circuit 74 and is used in turning the transistor 130 on and off. A resistor 140 connected between the leads 134 and 138 provides a forward bias between the emitter-base junction of transistor 130 such that grounding of the control lead 138 can occur through any of several circuits including the circuits that include any one of resistors 142, 144 or 146. This therefore provides various possibilities for turning on of the transistor 130 to energize the relay coil 112.

Turning now to the sensor circuit 74, the resistive element 29 of the sensor 14 is connected between terminals 2 and 3 of the female connector 136, and the heater element 30 of the sensor 14 is connected between terminals 1 and 3 of the connector 136 as shown in FIG. 4B. Terminal 2 of the connector 136 is the output connection of the sensor 14 and is grounded through a resistor 148 and a diode 150. Terminal 1 of the connector 136 is also connected to ground through the diode 150 as shown. Once the sensor 14 stabilizes after initially being turned on, the current output of the sensor 14 is dependent on the presence of free oxygen and certain exhaled gases in the air passing around the sensor 14. The breath of a patient when he exhales is characterized by a depletion of free oxygen and an increase in the amount of other gases which will lower the resistance of the resistive element 29 in the sensor 14. This will increase the current flowing out at the terminal 2 of the connector 136. Thus when the patient exhales, the voltage across the resistor 148 and the diode 150 will increase. The voltage drop across the resistor 148 and the diode 150 is the voltage output of the sensor 14. The female connector 136 receives the male connector of plug 44.

Terminal 2 of the connector 136 is also connected to the anode of a zener diode 152 which has its cathode connected to the common sides of resistors 154 and 156. The other side of the resistor 154 is connected to a positive terminal 158 and the other side of the resistor 156 is connected to the base element of a transistor 160. The emitter of the transistor 160 is connected to one side of a resistor 162, the opposite side of which is grounded. The collector of the transistor 160 is connected to the control lead 138 of the relay circuit 72 through the resistor 144. Thus it can be seen that when the transistor 160 is turned on, current will flow from the base of the transistor 130 through the resistors 144 and 162 to ground, turning on the transistor 130 and energizing the relay coil 112.

The positive voltage at the terminal 158 reverse biases the zener diode 152 above its zener voltage throughout the range of the output voltages produced by the sensor 14. It will thus be understood that the voltage applied to the base of the transistor 160 includes the output voltage of the sensor 14 plus the voltage across the resistor 148 due to the reverse current flowing throughout the zener diode 152 added to the zener voltage of the diode 152. If this voltage is higher than the voltage which appears at the emitter of the transistor 160, the transistor 160 will turn on and the relay coil 112 will be energized as previously explained. The voltage at the emitter of the transistor 160 is determined by the output current of a transistor 164 flowing through the resistor 162. It is therefore necessary to understand the operation of the transistor 164. The base of the transistor 164 is connected to the adjustable tap of a potentiometer 166, the collector of the transistor 164 is connected to the high potential side 168 of the potentiometer 166, and the emitter of the transistor 164 is connected to the emitter of the transistor 160 and also to one side of the resistor 162. This circuit construction reverse biases the collector-base junction of the transistor 164 and forward biases the base-emitter junction placing the transistor 164 in its active operating region.

Thus, changing the setting of potentiometer 166 by means of the control 60 shown in FIG. 3, changes the amount of current from the transistor 164 that flows through the resistor 162, thereby also effecting the voltage at the emitter of the transistor 160.

It can thus be seen that the transistors 160 and 164 form the voltage comparator circuit 76 wherein the varying or operative portion of the comparison voltage which appears on the base of the transistor 160 is the output voltage produced by the sensor 14. This voltage which is referred to as the comparison voltage is compared to a threshold voltage which is established by the setting of the potentiometer 166. When the comparison voltage is greater than the threshold voltage, the transistor 160 will turn on or conduct to energize the relay coil 112. The control 60 of potentiometer 166 is adjusted for each individual patient being monitored to make sure than the relay circuit 72 switches each time the patient exhales. This control provides that not only will the warning buzzer 84 be sounded if the patient's breathing ceases or slows below a rate established by the setting of the control 58 as described, but that the warning buzzer 84 will also sound if the gas components of the patient's breath when he exhales do not raise the output voltage of the sensor 14 sufficiently to exceed the threshold voltage established by the setting of the control 60 indicating that the patient's ability to use free oxygen during breathing is decreasing. This is an important bodily function that has not heretofore been easily or accurately monitored.

In the case of a patient who begins to breathe very rapidly, if the accelerated rate of breathing floods the gas sensor 14 with exhaled gases resulting in the comparison voltage on the base of transistor 160 not dropping below the threshold voltage on the emitter of the transistor 160 when the patient inhales, and if this condition persists for a period of time longer than the period of time determined by the setting of control 58, the warning buzzer 84 will be energized by the exhale delay circuit 80 to give a warning. If, on the other hand, the gas composition of the patient's exhaled breath during this condition is not sufficient to give a comparison voltage higher than the threshold voltage as described, the inhale delay circuit 82 will remain energized, and if this condition persists for a period of time longer than the period of time determined by the setting of control 58, the warning buzzer 84 will be energized by the inhale delay circuit 82 to give a warning.

The open-sensor warning circuit 78 includes other transistors 170 and 172 connected as shown. The base of the transistor 170 is connected to terminal 2 of the sensor connector 136 through a resistor 174, the emitter of the transistor 170 is grounded, and the collector is connected to the base of the transistor 172 and also to the positive voltage supply lead 134 through a resistor 176. The emitter of the transistor 172 is grounded and its collector is connected to the control lead 138 of the relay circuit 72 through the resistor 146. As long as there is output current from terminal 2 of the connector 136, the transistor 170 will be turned on, grounding the base of the transistor 172 and holding the transistor 172 in its cutoff condition. If the sensor 14 is disconnected from connector 136 or if sensor 14 fails in an open circuit condition, the transistor 170 will turn off and the transistor 172 will turn on grounding the base of the transistor 130 through the resistor 146 thereby turning on the transistor 130 and energizing the relay coil 112. This will place the movable relay contact 114 in position to activate the exhale delay circuit 80.

If on the other hand the sensor 14 fails in the shorted condition, the voltage output thereof will rise to the positive supply voltage, turning on the transistor 160 and energizing the relay coil 112 and placing the movable contact 114 in position to activate the exhale delay circuit 80. Either type failure of the sensor 14 will hold the control circuit 34 in the exhale mode until the failed sensor is replaced or the trouble in the circuit is remedied.

A relay test switch 178 is connected between ground and the control lead 138 through the resistor 142. Closing the relay test switch 178 energizes the relay coil 112 thereby switching the movable contact of the relay contacts 114 to operation with the exhale delay circuit 80 instead of the inhale delay circuit 82 and is used to test the operation of the relay circuit 72. The relay test switch 178 is included as the switch portion of the element 52 of FIG. 3.

The exhale delay circuit 80 and the inhale delay circuit 82 are similar in construction and are connected to the relay contacts 114 by control leads 180 and 182 respectively. The movable contact of the relay contacts 114 is connected to the positive side of the power supply 88 through the switch 90, and the relay contacts 114 connects one or the other of the control leads 180 and 182 to the positive power supply depending upon the condition of the relay coil 112. When the relay coil 112 is deenergized, the inhale delay circuit 82 is connected to the positive power supply, and when the relay coil 112 is energized the exhale delay circuit 80 is so connected.

The exhale delay circuit 80 includes a light source 184 which is energized whenever the control lead 180 is connected to the positive power supply for indicating that a monitored patient is exhaling. The light source 184 is identified as element 50 in FIG. 3. The control lead 180 is connected to the base of a transistor 186 through a resistor 188. The emitter of the transistor 186 is grounded, and the collector is connected to a positive voltage supply terminal 190 through a resistor 192. Also connected to the positive terminal 190 through the resistor 192 is a diode 194 which is connected to charge a capacitor 196 when the transistor 186 is turned off. The charging of the capacitor 196 from the terminal 190 through the resistor 192 and the diode 194 almost immediately turns on another transistor 198 whose collector is connected to the base of still another transistor 200 such that when the transistor 198 turns on, the base of the transistor 200 is grounded holding the transistor 200 in its cutoff condition. When the transistor 186 is turned on, the anode of the diode 194 is grounded, and the diode 194 no longer conducts. As a result the capacitor 196 begins to discharge through a resistor 202 and the base-emitter junction of the transistor 198 and through a potentiometer 204 at a rate controlled by the setting of the potentiometer 204. When the capacitor 196 has sufficiently discharged, the transistor 198 will turn off, turning on the transistor 200, and completing a circuit to energize the warning buzzer 84 through a diode 206 when an on/off switch 208, identified as switch 64 in FIG. 3, is closed. A resistor 210 and a diode 212 are connected between the positive terminal 190 and the base and the collector of the transistor 200 respectively to hold the transistor 200 in the on condition after it has turned on. A light emitting diode 214 and a resistor 216 are provided between the collector of the transistor 200 and the positive voltage supply terminal 190 to give a visual indication when the exhale delay circuit 80 has completed the circuit to the warning buzzer 84 and the switch 208. The on/off switch 208 is located between the warning buzzer 84 and the delay circuits 80 and 82 to turn off the warning buzzer 84 during the start up period, as will be explained.

The control lead 182 of the inhale delay circuit 82 is connected both to a light source 218 and to the base of transistor 220 through a resistor 222. When the movable relay contact 114 is in electrical contact with the lead 182, the transistor 220 is turned on. The light source 218 is the inhale indicator light portion of the element 52 shown in FIG. 3. A capacitor 224 is charged through a diode 226 and a resistor 228 from a positive supply terminal 230 almost immediately turning on a transistor 232 whose emitter is connected to the base of still another transistor 234 thereby holding the transistor 234 in its cutoff condition. When the transistor 220 is turned on, the anode of the diode 226 is grounded and the capacitor 224 begins to discharge through a resistor 236 and the base-emitter junction of the transistor 232 and through a potentiometer 238 at a rate controlled by the setting of the potentiometer 238. When the capacitor 224 is discharged sufficiently, the transistor 232 turns off, turning on the transistor 234 to complete the circuit to energize the warning buzzer 84 through a diode 240 when the switch 208 is closed. A resistor 242 and a diode 244 are supplied between the positive terminal 230 and the base and the collector of the transistor 234 respectively to hold the transistor 234 in the on condition once it has been turned on. A light emitting diode 246 is connected in series with a resistor 248 between the collector of the transistor 234 and the positive supply terminal 230 to give a visual indication when the inhale delay circuit 82 has completed the circuit to the warning buzzer 84 and the switch 208. It can thus be seen that the light source 218 is turned on immediately upon connection of the control lead 182 to the positive supply of power supply 88 through relay contacts 114. After a preset time period which is determined by the setting of potentiometer 238, the light emitting diode 246 is turned on and, if switch 208 is closed, the warning buzzer 84 is energized.

The potentiometers 204 and 238 are ganged together as shown by dotted lines 250 such that both of the potentiometers 204 and 238 are adjusted together so that the discharge rates of the capacitors 196 and 224 are identical. The control of the ganged potentiometers 204 and 238 is shown as the adjustable control 58 in FIG. 3.

Delay circuit test switches 252 and 254 allow the testing of the components of the delay circuits 80 and 82, and are connected such that both of the switches 252 and 254 are operated together. The normal positions of switches 252 and 254 are shown in FIG. 4B wherein the switch 252 is closed and the switch 254 is opened. When the switch 252 is opened, any current flowing through the relay coil 112 is interrupted such that the movable relay contact 114 goes to its normal position as shown wherein the control lead 182 is connected to the positive power supply. Closing the switch 254 connects the control lead 180 to the positive power supply. Thus switching the delay circuit test switches 252 and 254 to their transferred positions energizes both of the inhale and the exhale delay circuits 80 and 82, energizing their respective light sources 184 and 218 and turning off the the transistors 186 and 220 to begin the discharge of the capacitors 196 and 224. After the time period set by the potentiometers 204 and 238, the light emitting diodes 214 and 246 are turned on, and the warning buzzer 84 will be energized if the switch 208 is closed thereby giving a positive test to the elements of the delay circuits 80 and 82.

The meter scale adjustment 56 and the meter 54 shown in both of FIGS. 3 and 4B are provided to measure the voltage drop across the resistor 148 and the diode 150 of the sensor circuit 74 as shown. The meter scale adjustment 56 includes a three position switch member 256 which switches different value resistors 56A, 56B, and 56C in series with the meter 54 to change the meter scale. A recording type voltmeter may optionally be used in place of voltmeter 54 to make a permanent recording of the excursions of the output voltage of the sensor 14. Such recordings may be studied by a physician to determine the breathing rate of a monitored patient, the deepness of his breaths, and other characteristics of the patient's breathing.

The respiration rate counter circuit 86 of FIG. 4A is connected to count the number of operations of the relay circuit 72 over a period of time such as over a minute, and includes means to display the resultant number. The circuit 86 is optional and is in addition to, or in lieu of, the meter 54. The respiration rate counter circuit 86 has a lead 258 connecting the control lead 180 to a multiplier circuit 260 whose output is connected to the input of a counter circuit 262. The counter circuit 262 counts the number of output pulses it receives from the multiplier circuit 260 and supplies this number at its output terminals in a binary coded decimal format. The output terminals of the counter circuit 262 are connected to a latch circuit 264 which accepts and stores the binary number it receives from the counter circuit 262, and drives a digital display device 266 to display this number. A clock input 268 is connected through a delay circuit 270 to the reset of the counter circuit 262. The clock input 268 is also connected to store input 271 of the latch circuit 264. The clock input 268 issues a train of time spaced clock pulses. Each clock pulse causes the latch circuit 264 to enter and store the number present at the output terminals of the counter circuit 262. A set period of time after each clock pulse from the clock input 268, the delay circuit 270 pulses the reset input of the counter circuit 262 to reset the number in the counter circuit 262 to zero thereby starting the counting cycle over again. The time delay of the delay circuit 270 allows the latch circuit 264 sufficient time to store the number present at the output terminals of the counter circuit 262 before the counter circuit 262 is reset.

The multiplier circuit 260 multiplies the number of operations of the relay circuit 72 in accordance with the period of time between pulses of the clock input 268 in order to display the respiration rate in breaths per minute. For instance, if the period of the clock input 268 is thirty seconds, the multiplier circuit 260 will multiply by two because there are two thirty second periods per minute. A recording display device 272 may be used instead of or in conjunction with the digital display device 266 to make a permanent record of the respiration rate of the patient.

The lead 258 could be connected to the control lead 182 instead of the control lead 180 as shown. In that instance, the respiration rate circuit 86 would count and display a number related to the number of times the patient inhales rather than a number related to the number of times the patient exhales.

When the power switch 90 is first closed, the light 92 is illuminated and the capacitor 98 begins to charge turning on the transistors 104 and 108 thereby energizing the relay coil 112 to switch the movable contact of the relay contacts 114 from operation with the inhale delay circuit 82 to operation with the exhale delay circuit 80. The activation of the relay circuit 72 energizes the exhale light source 184 and turns on the transistor 186. Since the capacitor 196 is not charged at this time, the transistor 198 will be in the off condition allowing the transistors 200 to turn on thereby completing the circuit to the light emitting diode 214 and energizing the warning buzzer 84 if the switch 208 is closed. The switch 208 may be opened if desired so that the alarm buzzer 84 is not energized during the turn-on sequence.

The energizing of the relay coil 112 allows the capacitor 224 of the inhale delay circuit 82 to be charged almost instantly turning on the transistor 232 and holding the transistor 234 and the light emitting diode 246 in their off conditions. Simultaneously with the charging of the capacitor 224, the capacitors 116, 120 and 98 of the turn-on circuit 70 begin to charge. When the capacitor 120 has charged sufficiently, the transistor 124 will turn on thereby turning on the transistor 126 grounding the anode of the diode 102. The capacitor 98 then begins to discharge through the base-emitter junction of the transistor 104 until the transistor 104 is turned off, thereby turning off the transistor 108 and deenergizing the relay coil 112. This returns the movable relay contact 114 back to operation with the inhale delay circuit 82 and starts the operation of the breath monitor circuit in its breath sensing function. The time delay provided by the turn-on circuit 70 thus gives sufficient time for the capacitor 224 to charge and for the sensor 14 to be stabilized.

Once the turn-on function is complete, the voltage comparator circuit 76 may be adjusted by adjusting the control 60 of the potentiometer 166 to set the threshold voltage on the base of the transistor 160 to be just below the comparison voltage on the emitter of the transistor 160 such that the movable relay contact 114 will switch from operation with the inhale circuit 80 to operation with the exhale circuit 82 each time the patient exhales. The alarm rate adjustment is made by adjusting the control 58 of the potentiometers 204 and 238 to the minimum number of breaths the patient must take per minute before the alarm is sounded. The alarm switch 208 may then be moved to the on condition to place the warning buzzer 84 in the circuit. The respiration rate counter circuit 86 then counts, displays and/or records the breaths per minute taken by the patient.

The meter scale switch 56 is also adjusted such that the meter 54 displays and/or records the output voltage of the sensor 14. When the control circuit 34 is first turned on, the sensor output voltage will commence to rise until the sensor heating element 30 heats the resistive sensor element 29 to some desired operating temperature. Once the resistance of the element 29 is stabilized for the ambient air conditions, the output voltage of the sensor 14 will stabilize at some normal level. This stabilized voltage can be observed on the meter 54 and should occur before the turn-on cycle of the turn-on circuit 70 is complete. After the cycle of the turn-on circuit 70 is complete, the relay circuit 72 should be in its normal operating condition with the inhale light source 218 of the inhale/test element 52 energized as previously described.

If the sensor 14 fails in either the shorted or in the open circuit condition the relay coil 112 will remain energized as aforesaid, and the movable relay contact 114 will not switch from operation of the exhale circuit 80 to operation of the inhale circuit 82. The type of failure of the sensor 14 in either case may also be determined by observing the meter 54. If the sensor 14 has failed in the shorted condition, the meter 54 will show a high voltage reading, and if the sensor 14 has failed in the open circuit condition, the meter 54 will show no voltage.

The remote monitor connector 45 shown in FIG. 1 has a number of conductors one of which is connected to circuit location 274 for supplying a voltage to a remote light source for being energized when the control circuit 34 is turned on. The remote connector 45 also has a conductor connected to circuit connected point 276 for supplying a voltage to a remote exhale indicator and respiration rate counter circuit when the exhale delay circuit 80 is energized, a conductor connected to circuit point 278 for supplying a voltage to a remote inhale indicator when the inhale delay circuit 82 is energized, and a conductor connected to circuit point 280 for completing the circuit to a remote warning device for sounding a warning at the remote location such as at a nurses station when the warning buzzer 84 is energized as earlier described. The remote connector 45 also includes a conductor connected to circuit point 282 (FIG. 4B) for connecting to a remote voltage measuring and/or recording device (not shown) to allow remote monitoring of the output voltage of the sensor 14, and a conductor connected to point 284 for providing a remote relay test switch for remote testing of the relay circuit 72 such as described in conjunction with the relay test switch 178. An optional remote control switch 286 can also be provided to switch out the circuit of transistor 164, and switch in a similar circuit (not shown) connected to circuit lead 287 and located at the remote location to provide for setting the threshold voltage of the comparator circuit 76 from the remote location. Other optional remote control switches can also be included in control circuit 34 at points 288 and 290 to switch the breathing rate adjustment of control 58 of the circuit 34 to the remote location if desired. These switches (not shown) can also be connected at points 288 and 290 to allow for switching in a pair of remotely positioned ganged potentiometers similar to the potentiometers 204 and 278 to be used remotely to change the delay period of the circuits 80 and 82 as described earlier. This would be in place of the potentiometers 204 and 238.

Although the circuit and circuit operation are shown and described in terms of discrete circuit components and their operation, the circuit could be constructed using integrated circuitry or other technologies without departing from the basic concepts. The various functions of the circuit could also be embodied in a microprocessor.

Thus there has been shown and described a breath monitor device which fulfills all of the objects and advantages sought therefor. It will be apparent to those skilled in the art, however, that many changes, modifications, variations, and other uses and applications for the subject device are possible. All such changes, modifications, variations and other uses and applications which do not depart from the spirit and scope of the invention are deemed to be covered by the invention which is limited only by the claims which follow.

What is claimed is:

1. A breath monitor device comprising means for sensing the chemical composition of exhaled gases and inhaled gases of a patient, means responsive to said sensing means for timing the respective intervals between successive sensed exhaled gases and between successive sensed inhaled gases and means responsive to said timing means, including means for generating a warning signal when at least one of the sensed intervals exceeds a predetermined time.

2. The breath monitor device of claim 1 further comprising means responsive to said sensing means for separately indicating the exhaling and inhaling of a patient being monitored.

3. The breath monitor device of claim 2 further comprising counting means including means for counting at least one of the exhalings and inhalings of a patient in a preselected time period, and display means including means for displaying the number counted by said counting means.

4. The breath monitor device of claim 1 wherein said timing means includes means for adjusting the duration of the predetermined time interval.

5. The breath monitor device of claim 1 further comprising comparator means operatively connected to said sensing means, said comparator means including adjustment means adjustable to establish a threshold condition which when exceeded by the output of the sensing means distinguishes between inhalings and exhalings of the patient.

6. The breath monitor device of claim 5 wherein said comparator means includes a zener diode.

7. A breath monitor device for use with an apparatus assisting the breathing of a patient, said breath monitor device comprising;
sensor means located in said breath assisting apparatus to respond to the breathing of the patient and for sensing utilization of gases being breathed by a patient;
relay means including associated circuit means energizable and deenergizable in response to said sensor means, said relay means having a first condition when said sensor means senses inhaled gases and a second condition when said sensor means senses at least a a preset change in the oxygen of the exhaled gases from the inhaled gases when the patient is exhaling;
an inhale circuit operatively connected to said relay means including an indicator which is energized when said relay means is in its first condition;
a first time delay circuit operatively connected to the relay means, said first time delay circuit having a first operative condition which occurs while the relay means is in its first condition and a second operative condition for a first predetermined period of time after the relay means is in its second condition for the first predetermined length of time;
an exhale circuit operatively connected to said relay means including an indicator which is energized when said relay means are in its second condition;
a second time delay circuit operatively connected to the relay means, said second time delay circuit having a first operative condition which occurs while the relay means is in its second condition for a second predetermined period of time and a second operative condition after the relay means has been in its first condition for the second predetermined length of time; and
warning signal means operatively connected to said first and second time delay circuits, said warning signal means being deenergized when said first and second time delay circuits are in their respective first operative conditions and said warning signal means being energized to produce a warning condition when at least one of said first and second time delay circuits is in its second operative condition.

8. The breath monitor device of claim 7 further comprising adjustable means operatively connected to said first and second time delay circuits, said adjustable means including means having a plurality of setting positions for simultaneously changing the predetermined times associated with said first and second time delay circuits.

9. The breath monitor of claim 7 further comprising comparator means operatively connected to an output of said sensor means, said comparator means including adjustment means adjustable for establishing a threshold condition which, when exceeded by said sensor means output, distinguishes changes of the exhaled and inhaled gases from a preset level.

10. The breath monitor device of claim 9 wherein said comparator means includes a zener diode.

11. The breath monitor device of claim 7 further comprising a remote unit at a location removed from the patient being monitored and operatively connected to said relay means and to said first and second time delay circuits, said remote unit including a second inhale indicator which is energized when said relay means is in its first condition, a second exhale indicator energized when said relay means is in its second condition, and second warning signal means deenergized whenever said first and second time delay circuits are in their respective first operating conditions, said second warning signal means being energized to produce a warning condition at the remote location when at least one of said first and second time delay circuits is in its second operating condition.

12. The breath monitor device of claim 7 further including counting means operatively connected to said relay means, said counting means including means for counting and storing the number of times said relay means changes from one of its conditions to the other of its conditions, and means operatively connected to said counting means including means for displaying the number stored by said counting means.

13. The breath monitor device of claim 12 further including means operatively connected to said counting means including means for periodically resetting the number stored by said counting means to some minimum condition, and means operatively connected to said counting means for displaying a number related to the number stored by said counting means representative of the number of breaths taken by the patient within a given period of time.

14. An apparatus for monitoring the breathing of a patient comprising a tracheal tube for installing in the throat of a patient whose breath is to be monitored, said tracheal tube having an open ended passageway therethrough for breath to pass during inhaling and exhaling, an adapter including means for attaching to the tracheal tube to form an extension of the passageway, said adapter having means therein forming a chamber adjacent the tube that communicates with the passageway, and a sensor element positioned in the chamber, said sensor element including means for producing an electric response which varies with the chemical composition of the gases moving through the passageway contacting the sensor element as the patient breathes.

15. The apparatus defined in claim 14 including electric circuit means operatively connected to the sensor element, said electric circuit means including a first circuit portion for responding to gases inhaled by the patient and a second circuit portion for responding to gases exhaled by the patient, and means responsive to predetermined changes in the electric responses produced by the sensor element for switching between actuation of the first and second portions.

16. The apparatus defined in claim 15 including means operatively connected to said means responsive to predetermined changes for counting the predetermined changes that take place in the sensor element.

17. The apparatus defined in claim 16 including means to reset the counting means at predetermined time intervals, and means to display the count in the counting means.

18. The apparatus defined in claim 15 including means for establishing a predetermined threshold level for the electric response produced by the sensor element and means for comparing the electric response produced by the sensor element with said predetermined threshold level.

19. A breath monitor device comprising:
a breathing assistance apparatus having an air passage through which a patient breathes, said breathing assistance apparatus having means allowing access to the air passage,
a sensor circuit having an electric sensing element the impedance of which decreases in the presence of exhaled gases as compared to inhaled gases located in the air passage so that gases breathed by the patient pass adjacent to and in contact with the sensing element, said sensor circuit including an output having a relatively high voltage when the sensing elements senses exhaled gases and a relatively low voltage when the sensing element senses inhaled gases,
a voltage comparator circuit connected to the output of said sensor circuit including means for producing a threshold voltage, means for adjusting the level of said threshold voltage, means for comparing the output voltage of the sensor circuit with the threshold voltage, and a comparator output terminal, said comparator circuit producing a first voltage condition on the output terminal when said sensor circuit output voltage is higher than the threshold voltage and a second voltage condition on the comparator output terminal when said sensor circuit output voltage is less than the threshold voltage,
a relay circuit having an input connected to the comparator output terminal of the voltage comparator circuit, said relay circuit including means for going between first and second operating conditions in response respectively to the presence of the first and second voltage conditions at the comparator output terminal,
an exhale circuit including an exhale time delay circuit operatively connected to the relay circuit, said exhale time delay circuit including means for establishing a predetermined first delay time period,
an inhale circuit including an inhale time delay circuit operatively connected to the relay circuit, said inhale time delay circuit establishing a second predetermined delay time period,
said exhale circuit being operative when said relay circuit is in its first operating condition, and said inhale circuit being operative when the relay circuit is in its second operating condition,
a warning device having operative connections to the exhale and to the inhale time delay circuits, said warning device being deenergized before the expiration of either of the first or second predetermined delay time periods, and being energized upon the expiration of either of the first or second predetermined delay time periods.

20. The breath monitor device of claim 19 wherein said exhale time delay circuit has a first operating condition between the energizing of said exhale circuit and the expiration of said predetermined first delay time period and a second operating condition after the expiration of said predetermined first delay time period, said inhale time delay circuit having a first operating condition between the energizing of said inhale circuit and the expiration of said predetermined second delay time period and a second operating condition after the expiration of said predetermined second delay time period, said warning device being deenergized whenever said inhale and exhale time delay circuits are in their first operating conditions, and said warning device being energized whenever at least one of said exhale and inhale time delay circuits is in its second operating condition.

21. The breath monitor device of claim 20 wherein said exhale and inhale time delay circuits each includes respective indicating means energizable when its respective time delay circuit is in its second operating condition.

22. The breath monitor device of claim 19 including exhale indicator means operatively connected to said relay circuit and energizable when said relay means is in its first operating condition, and inhale indicator means operatively connected to said relay circuit and energizable when said relay means is in its second operating condition.

23. The breath monitor device of claim 11 wherein said warning device includes means for producing an audible warning signal.

24. The breath monitor device of claim 14 wherein said voltage comparator circuit includes a zener diode.

25. The breath monitor device of claim 19 including a remote unit at a location removed from the patient whose breath is being monitored and operatively connected to said relay circuit and said inhale and exhale circuits, said remote unit having an exhale indicating means connected to said relay circuit and energizable when said relay circuit is in its first operative condition, an inhale indicating means connected to said relay circuit and energizable when said relay circuit is in its second operative condition, and a second warning device connected to the exhale and inhale time delay circuits producing a warning condition when energized, said second warning device being deenergized when said exhale and inhale time delay circuits are in their first operating conditions and being energized to produce a warning condition at the remote location when at least one of said exhale and inhale time delay circuits is in its second operating condition.

26. The breath monitor device of claim 19 including a test circuit operatively connected to the input of said relay circuit, said test circuit having a first operative condition allowing said relay circuit to be in one of its first and second operating conditions, and a second operative condition holding said relay circuit in its second operating condition.

27. The breath monitor device of claim 19 including a test circuit operatively connected to said exhale and inhale circuits for simultaneously energizing both of said inhale and exhale circuits.

28. The breath monitor device of claim 19 including adjustable means operatively connected to said exhale and inhale time delay circuits, said adjustable means having a plurality of settings for simultaneously controlling the predetermined operation of the time periods established by said exhale and inhale time delay circuits.

29. The breath monitor device of claim 19 wherein said electrical sensor circuit includes means for displaying the voltage output of said sensor circuit.

30. The breath monitor device of claim 29 wherein said voltage output displaying means includes means for recording the voltage output of said sensor circuit.

31. The breath monitor device of claim 19 including an open-sensor circuit operatively connected to the input of said relay circuit, said open-sensor circuit including means for holding said relay circuit in its second operating condition in absence of an output voltage of said sensing element.

32. The breath monitor device of claim 19 including a turn-on circuit operatively connected to said relay circuit for transferring the relay circuit to its first operating condition for a predetermined time after said turn-on circuit is initially energized, said relay circuit going to its second operating condition at the end of said predetermined time, and an on/off switch operatively connected between said warning device and said inhale and exhale circuits for deactivating the warning device the predetermined time after the turn-on circuit is energized.

33. The breath monitor device of claim 19 wherein said breathing assistance apparatus includes a tracheal tube.

34. The breath monitor device of claim 19 including counting means operatively connected to the relay circuit, said counting means including means for counting the number of times said relay circuit changes from one of its operating conditions to the other, and means operatively connected to said counting means for displaying a number representing the number of breaths taken in a preselected time interval.

35. The breath monitor device of claim 34 including means operatively connected to said counting means for periodically resetting the counting means to some predetermined count.

36. A breath monitor device comprising sensor means for sensing at least one gas component of the breath of a patient, support means for positioning said sensor means in the flow of breath of the patient, circuit means operatively connected to said sensor means including threshold means for determining the initial level of said breath gas component and comparator means responsive to changes in said breath gas component as sensed by the sensor means for indicating changes of said breath gas component from said initial level, means responsive to predetermined changes in the breath gas component as sensed by the sensor means for counting the breaths that occur per unit of time, and warning means responsive to said comparator means and to said means for giving a warning if the breath gas component changes from said initial level.

37. The breath monitor device of claim 36 wherein said sensor means includes a resistive element whose resistance has a first value in the presence of oxygen and whose resistance decreases in response to depletion of oxygen.

38. The breath monitor device of claim 36 wherein the sensor means includes a resistive element whose resistance changes depending on whether the patient is inhaling or exhaling, the direction of the change in the resistance of the resistive element changing at times when the patient changes between inhaling and exhaling.

39. A breath monitor device comprising sensing means in the air stream of a patient during at least one of exhaling and inhaling, said sensing means including means responsive to the composition of the breath, circuit means operatively connected to said sensing means including means for generating an output each time the sensing means senses a change in the composition of the breath as sensed by the sensing means due to the patient changing between inhaling and exhaling, counting means operatively connected to said circuit means including means for counting the changes sensed by the sensing means, and display means operatively connected to said counting means for displaying a number related to the number of changes that are counted in a predetermined time interval.

40. The breath monitor device of claim 39 wherein said circuit means includes reset means operatively connected to said counting means for resetting the counting means to some predetermined reset condition, and means to establish a predetermined time period between succeeding operations of the reset means.

41. The breath monitor device of claim 40 including means operatively connected to said counting means for recording the count therein.

42. An apparatus for monitoring the breathing of a patient comprising a tracheal tube for installing in the throat of a patient whose breath is to be monitored, said tracheal tube having an open ended passageway therethrough for breath to pass during inhaling and exhaling, an adaptor including means for attaching to the tracheal tube to form an extension of the passageway, said adaptor having means therein forming a chamber adjacent the tube that communicates with the passageway, a sensor element positioned in the chamber, said sensor element including means for producing an electric response which varies with the chemical composition of the gases moving through the passageway contacting the sensor element as the patient breathes, electric circuit means operatively connected to the sensor element, said electric circuit means including a first circuit portion for responding to gases inhaled by the patient and a second circuit portion for responding to gases exhaled by the patient, other circuit means including means responsive to predetermined changes in the electric response produced by the sensor element for switching between actuation of the first and second portions, each of said first and second circuit portions including time delay means, and an alarm device operatively connected to at least one of said first and second circuit portions, said one of said first and second circuit portions including means to energize the alarm device whenever the time of duration of the inhaled or exhaled gases associated with said second circuit portion exceeds some predetermined time period as established by the associated time delay means.

43. The apparatus defined in claim 42 including means operatively connected to said other circuit means for counting the predetermined changes that take place in the sensor element.

44. The apparatus defined in claim 43 including means to reset the counting means at predetermined time intervals, and means to display the count in the counting means.

45. The apparatus defined in claim 42 including means for establishing a predetermined electric response, and means for comparing the electric response produced by the sensor element with said predetermined threshold level.

46. A breath monitor device comprising sensor means for sensing at least one gas component of the breath of a patient, support means for positioning said sensor means in the flow of breath of the patient, circuit means operatively connected to said sensor means including threshold means for determining the initial level of said breath gas component and comparator means responsive to changes in said breath gas component as sensed by the sensor means for indicating changes in said breath gas component from said initial level, and warning means responsive to said comparator means for giving a warning if the breath gas component changes from said initial level, said sensor means including a resistive element whose resistance has a first value in the presence of oxygen and whose resistance decreases in response to depletion of oxygen, said threshold means including means for establishing a threshold voltage, said comparator means including a voltage comparator circuit having an input operatively connected to said sensor means, said input having an input voltage which varies inversely with the decrease in resistance of the resistive element, and said warning means producing a warning condition whenever the input voltage as determined by the resistance of the resistive element is less than said threshold voltage.

47. The breath monitor device of claim 46 wherein said voltage comparator circuit includes a zener diode connected in circuit with the resistive element.

48. The breath monitor device of claim 46 including timing circuit means operatively connected to the warning means, said timing circuit means including means for establishing a predetermined period of time, said warning means producing a warning condition whenever the input voltage is less than the threshold voltage at least once within said predetermined period of time.

49. The breath monitor device of claim 48 including means in the timing circuit means adjustable to establish the predetermined time period.

50. A method of monitoring breathing comprising providing a passageway for the flow of breath by a patient during inhaling and exhaling passing the breath as it flows through the passageway in contact with means which are responsive to the oxygen content of exhaled and inhaled gases, providing means associated with the responsive means to enable distinguishing between when the patient is inhaling and when exhaling based on the oxygen content of the breath, providing means for timing the intervals between successive ones of said inhalings and successive ones of the exhalings, and producing a warning condition if any one of said time intervals exceed a respective predetermined time period.

51. A method for monitoring the composition of the breath during breathing comprising passing the exhaled breath through a passageway and adjacent to an element positioned therein in position to be exposed to the exhaled breath, which element produces a response that is related to the chemical composition of the breath, establishing a threshold condition for comparing with the response produced by said element, comparing to said threshold condition the response produced by the element, and producing a warning when the comparison has a particular relationship.

* * * * *

UNITED STATES PATENT OFFICE
CERTIFICATE OF CORRECTION

Patent No. 4,366,821                    Dated January 4, 1983

Inventor(s) Edward A. Wittmaier & Joseph A. Kretschmer

It is certified that error appears in the above-identified patent and that said Letters Patent are hereby corrected as shown below:

Column 12, line 17, "connected" (second occurrence) should be --connection--.

Column 16, line 45, "11" should be --19--.

Column 16, line 47, "warming" should be --warning--.

Column 16, line 48, "14" should be --19--.

Signed and Sealed this

Fifteenth Day of March 1983

[SEAL]

*Attest:*

*Attesting Officer*

GERALD J. MOSSINGHOFF

*Commissioner of Patents and Trademarks*